United States Patent [19]

Ebmeyer et al.

[11] Patent Number: 5,756,840

[45] Date of Patent: May 26, 1998

[54] PROCESS FOR THE PREPARATION OF A PARTICULARLY PURE MONOCHLOROACETIC

[75] Inventors: Frank Ebmeyer, Augsburg; Detlef Kampmann; Ulf Otto Paulus-Von Russdorf, both of Gersthofen; Rudolf Rossmeissl, Mertingen, all of Germany

[73] Assignee: Hoechst Aktiengesellschaft, Germany

[21] Appl. No.: 763,512

[22] Filed: Dec. 11, 1996

[30] Foreign Application Priority Data

Dec. 11, 1995 [DE] Germany ............... 195 46 080.4

[51] Int. Cl.$^6$ ................................... C07C 51/00
[52] U.S. Cl. ........................................... 562/604
[58] Field of Search .............................. 562/604

[56] References Cited

U.S. PATENT DOCUMENTS 5,447,542  9/1995  Steiner et al. .

FOREIGN PATENT DOCUMENTS

| 0537838 | 4/1993 | European Pat. Off. . |
| 0453690 | 6/1994 | European Pat. Off. . |
| 1915037 | 10/1975 | Germany . |
| 4 313 121 | 8/1994 | Germany . |

OTHER PUBLICATIONS

*Ullmann's Encyclopedia of Industrial Chemistry*, 4th Ed., vol. 9, p. 395.

*Ullmann's Encyclopedia of Industrial Chemistry*, 1986 vol. 6, pp. 537, 539, 541, 552.

*Primary Examiner*—Samuel Barts
*Attorney, Agent, or Firm*—Connolly & Hutz

[57] ABSTRACT

The present invention relates to a process for the preparation of a particularly pure monochloroacetic acid, in which, in a first step, a hydrogenation of a mixture of mono- and dichloroacetic acid is carried out to a residual content of dichloroacetic acid of 400 to 600 ppm and, in a second step, this mixture is subjected to melt crystallization. The hydrogenation is carried out with a heterogeneous catalyst which comprises 0.1–5.0% by weight of palladium and in which active charcoal or silicon dioxide is used as the support.

9 Claims, No Drawings

PROCESS FOR THE PREPARATION OF A PARTICULARLY PURE MONOCHLOROACETIC

The present invention relates to a process for the preparation of a particularly pure monochloroacetic acid such as is required for the synthesis of base chemicals of the pharmaceutical industry and the cosmetics industry.

Monochloroacetic acid is prepared by direct chlorination of acetic acid. The undesirable by-product dichloroacetic acid is formed as an unavoidable product by hyperchlorination, and can be removed by distillation, crystallization or hydrogenation.

Because of the very similar boiling points (monochloroacetic acid: 189° C.; dichloroacetic acid: 194° C.), removal by distillation is expensive and uneconomical.

The removal of dichloroacetic acid from the crude monochloroacetic acid obtained after the chlorination by hydrogenation over a heterogeneous catalyst is known (for example in accordance with EP-A453 690, DE-A1915037 and EP-A-537838). If the dichloroacetic acid, which usually adheres to the crude monochloroacetic acid in a concentration of 2–5% by weight, is to be reduced to a concentration of <100 ppm, this requires long residence times of the crude monochloroacetic acid in the hydrogenation reactors or large catalyst volumes, i.e. the process becomes industrially expensive and cumbersome. Furthermore, the hydrogenation of monochloroacetic acid to acetic acid, which is an undesirable side reaction, occurs to an increased extent in such a procedure. It is appropriate industrially to operate the hydrogenation such that a decrease in the concentration of the dichloroacetic acid by a factor of 10, i.e., for example, from 3 to 0.3% by weight, and in exceptional cases, if very selective catalysts are used, even by a factor of 100, i.e., for example, from 3 to 0.03% by weight, is achieved. This procedure is described in the above publications.

The removal of dichloroacetic acid from the crude monochloroacetic acid by melt crystallization is furthermore known (Ullmanns Enzyklopädie der technischen Chemie [Ullmann's Encyclopedia of Industrial Chemistry], 4th edition, 1975, Volume 9, page 395). In this procedure, a decrease in the concentration of dichloroacetic acid by a factor of 4, i.e., for example, from 3 to 0.7–0.8% by weight, is achieved with a one-stage recrystallization. However, the space and time requirements of this process are considerable. In addition, after several crystallizations a mixture of monochloroacetic acid and dichloroacetic acid remains as the mother liquor, which still comprises at least 30% by weight of monochloroacetic acid, depending on the cooling conditions, which cannot be converted into a sellable product by further crystallization.

There was thus the object of providing a process for the preparation of a particularly pure monochloroacetic acid which does not have the disadvantages described above.

Surprisingly, a process has now been found for the preparation of a particularly pure monochloroacetic acid in which, in a first step, a hydrogenation of a mixture of mono- and dichloroacetic acid is carried out to a residual content of dichloroacetic acid of 400 to 600 ppm and, in a second step, this mixture is subjected to melt crystallization.

The process according to the invention allows very economical removal of the dichloroacetic acid obtained in the crude monochloroacetic acid with little industrial expenditure. By selective hydrogenation of the dichloroacetic acid, the undesirable formation of acetic acid is just as successfully avoided in this procedure as the production of highly concentrated mother liquor.

It was particularly surprising that a significant decrease in concentration was still achieved by melt crystallization even in the case of mixtures comprising less than 400 ppm of dichloroacetic acid. Normally, only significantly more highly concentrated mixtures are subjected to crystallization.

A heterogeneous catalyst which comprises 0.1–5.0, preferably 0.3–4, % by weight of palladium and active charcoal or silicon dioxide as the support is used for the hydrogenation. The BET surface area is 100–1300, preferably 500–1200, m$^2$/g.

The hydrogenation is carried out under an increased pressure of 0–10 bar, in particular 0–4 bar, and at a temperature of 100°–200° C., in particular 110°–150° C.

The process according to the invention is also suitable for mixtures having a very high content of dichloroacetic acid. Thus, even a eutectic mixture of monochloroacetic acid and 49% by weight of dichloroacetic acid can be purified without problems (cf. Example 3).

The crystallization is carried out as a melt crystallization without using a solvent. In a first step, a melt is first produced by heating, and this is then crystallized out by cooling in a second step. The crystallization process is carried out here such that dichloroacetic acid and other liquid or dissolved impurities remain in the residual melt and can be removed with it. For example, monochloroacetic acid having a residual content of only 80 ppm of dichloroacetic acid can be obtained by this process.

The following examples are intended to illustrate the invention without limiting it:

EXAMPLE 1

2 kg/hour of monochloroacetic acid having a dichloroacetic acid content of 3.2% by weight are passed together with 800 l/hour (STP) of hydrogen under an increased pressure of 1 bar and at a temperature of 130° C. over a fixed catalyst bed with a volume of 2 l in a tube reactor. An active charcoal with 0.5% by weight of Pd is used as the catalyst. The BET surface area is 1000 m$^2$/g. The product of this reaction, which comprises 0.6% by weight of dichloroacetic acid, is passed into a crystallizer and subjected to a single melt crystallization there. After this single recrystallization, the monochloroacetic acid comprises 0.15% by weight of dichloroacetic acid. The product is colorless and, in the molten state, water-clear.

EXAMPLE 2

Preparation of a particularly pure monochloroacetic acid: The procedure is as in Example 1, but the throughput of monochloroacetic acid in the hydrogenation is lowered to 1 kg/hour. A hydrogenation product which comprises 0.035% by weight of dichloroacetic acid is then obtained. After the recrystallization, the monochloroacetic acid comprises only 0.008% by weight of dichloroacetic acid. The product is likewise colorless and, in the molten state, water-clear.

EXAMPLE 3

The procedure is as in Example 2, but a monochloroacetic acid which comprises 49% by weight of dichloroacetic acid is used as the starting material and the throughput is lowered to 0.5 kg/hour. After hydrogenation, a product having a dichloroacetic acid content of 8% by weight remains. The product of the recrystallization still contains 2.2% by weight of dichloroacetic acid and is colorless and, in the molten state, water-clear. With these properties, it is outstandingly suitable as a starting material for the procedures described in Examples 1 and 2. A monochloroacetic acid of high quality can also be obtained from the eutectic mixture of monochloroacetic acid and dichloroacetic acid in this manner.

EXAMPLE 4

400 kg/hour of monochloroacetic acid having a dichloroacetic acid content of 3.1 % by weight are passed together with 15 m$^3$/hour (STP) of hydrogen under an increased pressure of 1 bar and at a temperature of 130° C. over a fixed catalyst bed having a volume of 800 l in a tube reactor. An active charcoal with 0.5% by weight of Pd is used as the catalyst. The hydrogenation product comprises 0.040% by weight of dichloroacetic acid. After recrystallization, the monochloroacetic acid comprises only 0.010% by weight of dichloroacetic acid. The product is colorless and, in the molten state, water-clear.

EXAMPLE 5

1 kg/hour of monochloroacetic acid having a dichloroacetic acid content of 22% by weight is passed together with 2600 L/hour (STP) of hydrogen under an increased pressure of 4 bar and at a temperature of 130° C. over a fixed catalyst bed having a volume of 2 l in a tube reactor. An active charcoal with 1.0% by weight of Pd is used as the catalyst. The BET surface area is 1000 m$^2$/g. The product of this reaction, which comprises 1.0% by weight of dichloroacetic acid, is passed into a crystallizer and subjected to a single melt crystallization there. After this single recrystallization, the monochloroacetic acid comprises 0.25% by weight of dichloroacetic acid. The product is colorless and, in the molten state, water-clear.

EXAMPLE 6

The procedure is as in Example 5, but the throughput of monochloroacetic acid in the hydrogenation is decreased to 0.5 kg/hour. A hydrogenation product which comprises 0.16% by weight of dichloroacetic acid is then obtained. After the recrystallization, the monochloroacetic acid comprises only 0.04% by weight of dichloroacetic acid. The product is also colorless and, in the molten state, water-clear.

We claim:

1. A process for the preparation of a high purity grade chloroacetic acid containing less than 200 ppm dichloroacetic acid, which comprises, in a first step, carrying out a hydrogenation of a mixture of mono- and dichloroacetic acid to a residual content of dichloroacetic acid of 400 to 600 ppm in the presence of palladium as a catalyst, and, in a second step, subjecting this mixture to melt crystallization.

2. The process as claimed in claim 1, wherein the catalyst comprises 0.1–5.0% by weight of palladium and in which active charcoal or silicon dioxide is used as the support.

3. The process as claimed in claim 2, wherein the catalyst comprises 0.3–4.0% by weight of palladium.

4. The process as claimed in claim 1, wherein the hydrogenation is carried out under an increased pressure of 0–10 bar.

5. The process as claimed in claim 1, wherein the hydrogenation is carried out under an increased pressure of 0–4 bar.

6. The process as claimed in claim 1, wherein the hydrogenation is carried out at a temperature of 100°–200° C.

7. The process as claimed in claim 1, wherein the hydrogenation is carried out at a temperature of 110°–150° C.

8. The process as claimed in claim 1, wherein a monochloroacetic acid which comprises 1–50% by weight of dichloroacetic acid is used as the starting material for the process.

9. The process as claimed in claim 8, wherein a monochloroacetic acid having a dichloroacetic acid content of 20–50% by weight is employed as the starting material and the hydrogenation is passed through twice before the melt crystallization.

* * * * *

UNITED STATES PATENT AND TRADEMARK OFFICE
CERTIFICATE OF CORRECTION

PATENT NO. : 5,756,840
DATED : May 26, 1998
INVENTOR(S) : FRANK EBMEYER ET AL

It is certified that error appears in the above-identified patent and that said Letters Patent is hereby corrected as shown below:

Cover page, in the title [54] "PROCESS FOR THE PREPARATION OF A PARTICULARLY PURE MONOCHLOROACETIC" should read -- PROCESS FOR THE PREPARATION OF A PARTICULARLY PURE MONOCHLOROACETIC ACID --.

Column 1, line 1, "PROCESS FOR THE PREPARATION OF A PARTICULARLY PURE MONOCHLOROACETIC" should read -- PROCESS FOR THE PREPARATION OF A PARTICULARLY PURE MONOCHLOROACETIC ACID --.

Signed and Sealed this

Eighth Day of December, 1998

Attest:

BRUCE LEHMAN

Attesting Officer

Commissioner of Patents and Trademarks